US009411034B2

(12) United States Patent
Hofstede et al.

(10) Patent No.: US 9,411,034 B2
(45) Date of Patent: Aug. 9, 2016

(54) MEASURING SYSTEM FOR NUCLEAR MAGNETIC MEASURING DEVICES

(71) Applicant: Krohne AG, Basel (CH)

(72) Inventors: Jan Johannes Jacobus Hofstede, Gouda (NL); Erwin Johannes Gerardus Bergkamp, Zeist (NL)

(73) Assignee: Krohne AG, Basel (CH)

( * ) Notice: Subject to any disclaimer, the term of this patent is extended or adjusted under 35 U.S.C. 154(b) by 533 days.

(21) Appl. No.: 14/076,609

(22) Filed: Nov. 11, 2013

(65) Prior Publication Data

US 2014/0132263 A1    May 15, 2014

(30) Foreign Application Priority Data

Nov. 14, 2012    (DE) .................... 10 2012 022 242
Mar. 7, 2013     (DE) .................... 10 2013 003 836

(51) Int. Cl.
| | | |
|---|---|---|
| *G01V 3/00* | (2006.01) | |
| *G01R 33/56* | (2006.01) | |
| *G01R 33/36* | (2006.01) | |
| *G01N 24/08* | (2006.01) | |

(52) U.S. Cl.
CPC ............ *G01R 33/56* (2013.01); *G01R 33/3621* (2013.01); *G01N 24/08* (2013.01); *G01R 33/3642* (2013.01)

(58) Field of Classification Search
USPC ........................................................ 324/309
See application file for complete search history.

(56) References Cited

U.S. PATENT DOCUMENTS

| | | | | |
|---|---|---|---|---|
| 5,903,150 A * | 5/1999 | Roznitsky | .......... | G01R 33/3657 324/318 |
| 6,420,873 B1 * | 7/2002 | Guthrie | .................. | G01R 33/56 324/318 |
| 7,076,283 B2 * | 7/2006 | Cho | ...................... | A61N 1/3702 128/901 |
| 8,106,905 B2 * | 1/2012 | Markowitz | ........... | A61B 5/0422 345/419 |
| 9,172,476 B2 * | 10/2015 | Nguyen | .............. | G01S 13/0209 |
| 2006/0020403 A1 | 1/2006 | Pusiol | | |
| 2009/0184712 A1 * | 7/2009 | Mallozzi | ................ | A61B 5/055 324/309 |
| 2012/0001629 A1 | 1/2012 | Hopper et al. | | |

FOREIGN PATENT DOCUMENTS

DE         3815419 A1    11/1989

OTHER PUBLICATIONS

Chen et al., "Biomedical Magnetic Resonance Technology", 1989, pp. 210-213, XP-002721493.

* cited by examiner

*Primary Examiner* — Walter L Lindsay, Jr.
*Assistant Examiner* — Frederick Wenderoth
(74) *Attorney, Agent, or Firm* — David S. Safran

(57) ABSTRACT

A measuring system for nuclear magnetic measuring devices having a controller, a signal generator and a signal processor with signal path having an input stage and a signal conditioner, interfering signals caused by the excitation signals and not occurring simultaneously with the measuring signals being received at an input of the input stage, the measuring signal having signal swing less than that of the interfering signal and the controller determining excitation signal output instants. A switch is located in the signal path between the input stage output and the signal conditioner input, and being switchable between first and second switching states by the controller. The controller switches the switch in the first switching state only in the periods in which there are no interfering signals at the input stage input, and a dynamic range of the signal conditioner input is adapted to the voltage swing of the measuring signals.

8 Claims, 1 Drawing Sheet

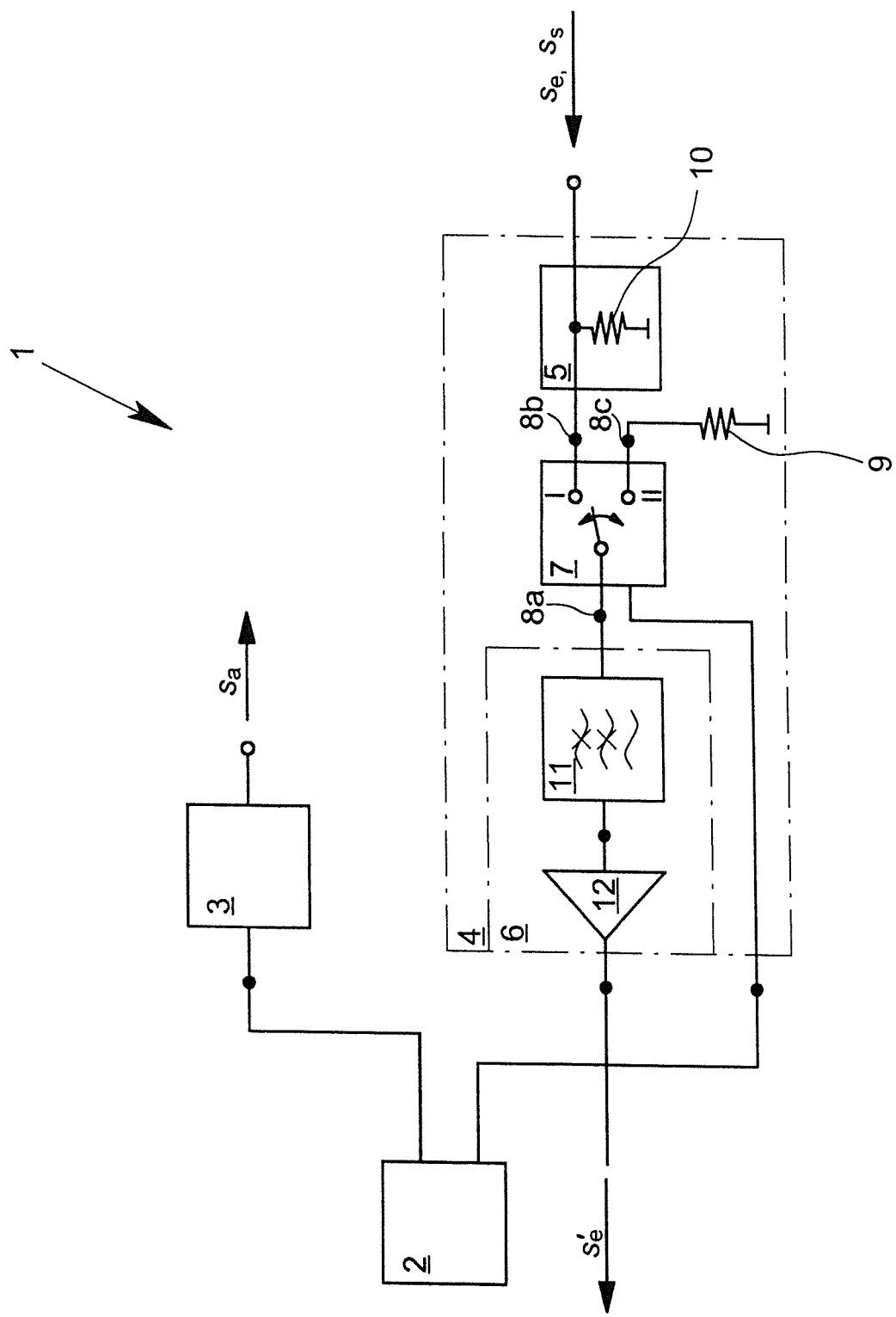

US 9,411,034 B2

MEASURING SYSTEM FOR NUCLEAR MAGNETIC MEASURING DEVICES

BACKGROUND OF THE INVENTION

1. Field of the Invention

The invention relates to a measuring system for nuclear magnetic measuring devices, having a controller, a signal generator for generating and outputting electric excitation signals $s_a$ and a signal processor with an input stage and a signal conditioner following the input stage in the signal path of the signal processor for processing the electric measuring signals $s_e$ effected by the excitation signals $s_a$ and being received at the input of the input stage, wherein interfering signals $s_s$ also effected by the excitation signals $s_a$ and not occurring simultaneously with the measuring signals $s_e$ are received at the input of the input stage, the signal swing of the measuring signal being less than the signal swing of the interfering signal and the controller determining the instants of time of outputting of the excitation signals.

2. Description of Related Art

The atomic nuclei of the elements having a nuclear spin also have a magnetic moment caused by the nuclear spin. The nuclear spin can be regarded as angular momentum describable by a vector, and accordingly, the magnetic moment can also be described by a vector, which is aligned parallel to the vector of the angular momentum. The vector of the magnetic moment of an atomic nucleus aligns in the presence of a macroscopic magnetic field itself parallel to the vector of the macroscopic magnetic field at the location of the atomic nucleus. The vector of the magnetic moment of the atomic nucleus precesses around the vector of the macroscopic magnetic field at the location of the atomic nucleus. The frequency of precession is the Larmor frequency $\omega_L$ and is proportional to the magnitude of the magnetic flux density B. The Larmor frequency is calculated according to $\omega_L=\gamma\cdot B$, $\gamma$ being the gyromagnetic ratio which is maximum for hydrogen nuclei.

Nuclear magnetic measuring devices implement nuclear magnetic resonance measuring methods. These measuring methods influence the precession of atomic nuclei of a medium in the presence of a macroscopic magnetic field by excitation using a controlled magnetic field and evaluate the effects of the influencing. Usually, the precession of the atomic nuclei is influenced by the measuring system, in that electrical excitation signals $s_a$ are generated. These electrical excitation signals $s_a$ can be converted to magnetic excitation signals in a transmitter coil, which influence the precession of the atomic nuclei. The electric signals usually induced in a sensor coil by the excited precessing atomic nuclei are used as fundamental quantity for the measuring methods. Often only a single coil is used as both transmitter coil and receiver coil.

An example of a nuclear magnetic measuring device is a nuclear magnetic flowmeter for multi-phase media that can measure the flow rate, which is the rate of flow of the individual phases of a medium and the proportions of the individual phases of the multi-phase medium. A prerequisite for measuring a multi-phase medium is that the individual phases of the medium can be excited to distinct nuclear magnetic resonances. Nuclear magnetic flowmeters can be used, e.g., for flow measurement of the multi-phase medium extracted from oil sources. This medium consists mainly of crude oil and salt water in the liquid phase and natural gas in the gaseous phase, wherein all phases contain the hydrogen nuclei necessary for nuclear magnetic resonance and can be excited to different nuclear magnetic resonances.

The measurement of the medium extracted from oil sources can be carried out using test separators. The extracted medium is fed into test separators for a period of time and they separate the individual phases of the medium from one another and determine the proportions of the individual phases of the medium. However, test separators, in contrast to nuclear magnetic flowmeters, are unable to reliably measure crude oil portions less than 5%. Since the proportion of crude oil of each source is steadily decreasing and the proportion of crude oil is already less than 5% in a plurality of sources, it is currently not possible to economically exploit these sources using test separators. In order to also further exploit sources with a very small proportion of crude oil, corresponding exact flowmeters are required for the medium consisting of several phases. In particular, nuclear magnetic flowmeters are a possible solution.

Adaptation of the maximum signal swing processable by the signal processor to the maximum signal swing of the measuring signal $s_e$ is required for a high accuracy of the measuring system. If the maximum swing of the measuring signals $s_e$ is less than the maximum signal swing processable by the signal processor, the measurement accuracy decreases. However, the sensor coil does not only receive the measuring signals $s_e$ effected by the excitation signals $s_a$, but also interference signals $s_s$ effected by the excitation signals $s_a$. Common among these interference signals $s_s$ is that they do not occur simultaneously with the measuring signals $s_e$ and the signal swing is greater than the signal swing of the measuring signals $s_e$. The excitation signals $s_a$, themselves, belong to the interference signals $s_s$. If only one single coil is used for both transmitting the excitation signals as well as for receiving measuring signals, interference signals $s_s$ are the same as excitation signals $s_a$.

Consequently, the maximum signal swing processable by the signal processor is either to be adapted to the maximum signal swing of the interference signal $s_s$ or the maximum signal swing at the input of the signal processor is to be limited. Adapting the maximum signal swing processable by the signal processor to the maximum signal amplitude of the interference signal $s_s$, however, decreases the measuring accuracy. Limiting the maximum signal swing at the input of the signal conditioner using a circuit with diodes is known from the prior art. Since, however, the forward voltage of diodes is greater than the signal swing of the measuring signals $s_e$, the maximum signal swing that can be processed by the signal processor is to be adapted to the forward voltage of the diodes and not to the maximum signal swing of the measuring signals $s_e$. This solution also leads to a reduction of the measuring accuracy.

SUMMARY OF THE INVENTION

The object of the present invention is, thus, to provide a measuring system that allows the adaptation of the maximum signal swing processable by the signal processor to the maximum swing of the measuring signal $s_e$ effected by the excitation signals $s_a$.

The measuring system according to the invention in which the previously derived and shown object is met, is initially and essentially wherein a switch is arranged in the signal path of the signal processor between the output of the input stage and the input of the signal conditioner, the switch being switchable to a first switching state I and a second switching state II by the controller, the signal at the output of the input stage being led to the input of the signal conditioner in the first switching state I, and the signal at the output of the input stage not being led to the input of the signal conditioner in the second switching state II, that the controller is designed to apply the switch in the first switching state I only in the periods of time, in which there are no interfering signals $s_s$ at the input of the input stage, and that the dynamic range of the input of the signal conditioner is adapted to the voltage swing of the measuring signals $s_e$.

The switch provided according to the invention allows precise adaptation of the maximum signal swing processable by the signal processor to the maximum signal swing of the measured signals $s_e$. In contrast to the switch with diodes known from the prior art, the attachment is not passive, but an active-controlled approach, wherein the implementation of the switch can include PIN diodes as switching elements. The passive attachment with diodes has the further disadvantage that the increase of the current through the diode only has a limited steepness with increasing voltage. Thus, in contrast to the active attachment according to the invention, interfering signals with arbitrarily high signal swings cannot be diverted away from the inlet of the signal processor.

According to a preferred design of the measuring system according to the invention, the periods of time in which the interfering signals $s_s$ are not present at the input of the input stage are determined taking into account the period between the instant of time of outputting one of the excitation signals $s_a$ from the signal generator and the instant of arrival of the interfering signals $s_s$ effected by the excitation signal $s_a$ at the input of the input stage. An electric excitation signal $s_a$ generated and output by the signal generator affects the precession of the atomic nuclei. The precession influenced by this excitation signal $s_a$ is retained in a measurement signal $s_e$. Since the time period between the output of an electric excitation signal $s_a$ and the input of the corresponding measuring signal $s_e$ is always constant, the switch is then only switched to the first switching state I, if only the measuring signal $s_e$ is applied to the input of the signal conditioner. In this manner, the interfering signals $s_s$ at the input of the input stage are diverted away from the signal conditioner.

In a particularly preferred design of the measuring system according to the invention, the switch is a single pole changeover switch with a middle terminal, a first terminal and a second terminal. The middle terminal is connected to the input of the signal conditioner, the first terminal is connected to the output of the input stage for guiding the signal at the output of the input stage to the input of the signal conditioner in the first state I, and the second terminal is connected to a constant potential via an ohmic mirror resistor for connecting the input of the signal conditioner to the mirror resistor in the second switching state II. The constant potential can, in particular, be the ground potential. As single-pole changeover switch, commercially available semiconductor switches known from the prior art that are controlled by the controller can be used. Using appropriate control signals, the controller can bring the changeover switch either into the first switching state I or into the second switching state II.

The mirror resistor provided in the design of the measuring system according to the invention last described guarantees that the input of the signal conditioner is also terminated in the second switching state II, so that no interfering signals can occur at the input of the signal conditioner. Having the switch in the second switching state II and not having the mirror resistor would lead to the input of the signal conditioner being high impedance and interferences could significantly affect the potential of the input. Interferences are dissipated by the mirror resistor.

Preferably, the signal path of the input stage is connected to a constant potential via an ohmic termination resistor such that the input resistance of the input stage corresponds to the resistance value of the termination resistor. The constant potential can, in particular, be the ground potential. The resistance value of the termination resistor can be selected to be equal to the line surge resistance value of the signal source, which leads the measuring signal $s_e$ to the input of the input stage. In this manner, reflections of the measuring signal $s_e$ are avoided at the input of the input stage.

Preferably, the resistance value of the mirror resistor and the resistance value of the termination resistor are selected such that the resistance value is independent of the switching state at the middle terminal of the changeover switch. Due to the circumstance that the signal input of the signal conditioner is always terminated with the same resistance value regardless of the switching state of the changeover switch, interference at the signal input of the signal conditioner can be avoided particularly well. If, for example, the signal input requires a constant direct current, different resistance values for the mirror resistor and the termination resistor would lead to different potentials at the signal input, in dependence of the switching state.

Cables with a line surge resistance of 50 ohms are widespread, so it is convenient to terminate the cable at the input of the input stage, in that the resistance value of the termination resistor is 50 ohms. In this way, reflections of the measuring signal $s_e$ are avoided at the input of the input stage. Consequently, it is also advantageous to select a resistance value of the mirror resistor of 50 ohms.

In a further preferred design of the measuring system according to the invention, the signal conditioner in the signal path includes a low-pass filter and an amplifier. The low-pass filter is arranged in the signal path between the input of the signal conditioner and the input of the amplifier and designed for attenuating interferences caused by switching the switch. Even if both the resistance value of the mirror resistor as well as the resistance value of the termination resistor are optimally selected, it is possible for interferences at the signal input of the signal conditioner to occur when the switch itself is switched. These interferences have in common that they essentially have a frequency spectrum that is above the frequency spectrum of the measuring signal $s_e$. Thus, it is possible to filter these interferences out using a low-pass filter, without, however, influencing the measuring signals $s_e$ in a negative way.

In detail, there are several possibilities for designing and further developing the measuring system according to the invention, as will be apparent from the embodiment described in the following and the accompany drawings.

BRIEF DESCRIPTION OF THE DRAWING

The sole FIGURE of the drawings is a diagram depicting a measuring system for nuclear magnetic measuring devices according to the invention.

DETAILED DESCRIPTION OF THE INVENTION

The essential elements of a measuring system 1 according to the invention for nuclear magnetic measuring devices comprises a controller 2, a signal generator 3 for generating and outputting electrical excitation signals $s_a$ and a signal processor 4. The signal processor 4 essentially comprises an input stage 5, a signal conditioner 6 and a switch 7, which is designed as a single-pole changeover switch. The switch 7 has a middle terminal 8a, a first terminal 8b and a second terminal 8c. The middle terminal 8a is connected to the input of the signal conditioner 6, the first terminal 8b is connected to the output of the input stage 5, and the second terminal 8c is connected to the ground potential via an ohmic mirror resistor 9.

In the first switching state I, the switch leads the signal incident at the output of the input stage 5 to the input of the signal conditioner 6, and in the second switching state II, the input of the signal conditioner 6 is connected to the ground potential via the mirror resistor 9. The switch 7 is switched by the controller 2 into either the first switching state I or into the second switching state II. The signal path of the input stage 5 is also connected to the ground potential via an ohmic termination resistor 10. Both the termination resistor 10 and the mirror resistor 9 have a resistance value of 50 ohms. This resistance value corresponds to the line surge resistance of the cable that leads the measuring signal $s_e$ to input of the input stage. Due to the selected resistance value of the termination resistor, reflections of the measuring signal $s_e$ are avoided at the input of the input stage 5. Due to the selection of the resistance value of the termination resistor 10 and the resistance value of the mirror resistor 9 of respectively 50 ohms each, the resistance value at the middle terminal 8a of the switch 7 is always 50 ohms, regardless of the switching state. In this manner, interferences at the input of the signal conditioner 6 are avoided.

The signal conditioner 6 essentially comprises a low-pass filter 11 and an amplifier 12. The low-pass filter 11 is arranged between the input of the signal conditioner 6 and the input of the amplifier 12. The corner frequency of the low-pass filter 11 is selected such that interferences caused by switching the switch 7 are filtered out. However, the corner frequency is selected so that the measuring signals $s_e$ are not affected. The conditioned measuring signals $s'_e$ are passed on for further processing, e.g., for digitization.

What is claimed is:

1. Measuring system for nuclear magnetic measuring devices, comprising:
   a controller,
   a signal generator for generating and outputting electric excitation signals and
   a signal processor with an input stage and a signal conditioner following the input stage in a signal path of the signal processor for processing the electrical measuring signals effected by the excitation signals and being received at an input of the input stage, wherein interfering signals also effected by the excitation signals and not occurring simultaneously with the measuring signals are received at the input of the input stage, a signal swing of the measuring signal being less than a signal swing of the interfering signal,
   wherein the controller determines instants of time of outputting of the excitation signals,
   wherein a switch is arranged in the signal path of the signal processor between an output of the input stage and the input of the signal conditioner, the switch being switchable to a first switching state I and a second switching state II by the controller,
   wherein the signal at the output of the input stage is led to the input of the signal conditioner in the first switching state I, and
   wherein the signal at the output of the input stage is not led to the input of the signal conditioner in the second switching state II,
   wherein the controller is adapted to switch the switch in the first switching state I only in periods of time in which there are no interfering signals at the input of the input stage, and
   wherein a dynamic range of the input of the signal conditioner is adapted to the voltage swing of the measuring signals.

2. Measuring system according to claim 1, wherein the controller is adapted to determine periods in which there are no interfering signals at the input of the input stage taking consideration the period of time between the instant of time of outputting of one of the excitation signals from the signal generator and the instant of time of arrival of the interfering signal effected by the excitation signals at the input of the input stage.

3. Measuring system according to claim 1, wherein the switch employs PIN diodes as switching elements.

4. Measuring system according to claim 1, wherein the switch is a single pole changeover switch with a middle terminal, a first terminal and a second terminal, the middle terminal being connected to the input of the signal conditioner the first terminal being connected to the output of the input stage for leading the signal at the output of the input stage to the input of the signal conditioner in the first switching state I, and the second terminal being connected via an ohmic mirror resistor to a constant potential for connecting the input of the signal conditioner to the mirror resistor in the second switching state II.

5. Measuring system according to claim 1, wherein the signal path of the input stage is connected to a constant potential via an ohmic termination resistor in such a manner that an input resistance value of the input stage corresponds to a resistance value of the termination resistor.

6. Measuring system according to claim 4, wherein the signal path of the input stage is connected to a constant potential via an ohmic termination resistor in such a manner that an input resistance value of the input stage corresponds to a resistance value of the termination resistor; wherein the resistance value of the mirror resistor and the resistance value of the termination resistor are selected such that the resistance value at the middle terminal is independent of the switching state of the switch.

7. Measuring system according to claim 6, wherein the resistance value of the mirror resistor and the resistance value of the termination resistor are 50Ω.

8. Measuring system according to claim 1, wherein the signal conditioner has a low-pass filter and an amplifier in the signal path and the low-pass filter is arranged in the signal path between the input of the signal conditioner and an input of the amplifier and is adapted to attenuate interferences effected by switching the switch.

* * * * *